(12) United States Patent
Chio (10) Patent No.: US 8,009,884 B2
(45) Date of Patent: Aug. 30, 2011

(54) METHOD AND APPARATUS FOR DIAGNOSING CONDITIONS USING TISSUE COLOR

(76) Inventor: Shiu-Shin Chio, Vista, CA (US)

( * ) Notice: Subject to any disclaimer, the term of this patent is extended or adjusted under 35 U.S.C. 154(b) by 1016 days.

(21) Appl. No.: 11/820,352

(22) Filed: Jun. 19, 2007

(65) Prior Publication Data

US 2008/0008370 A1    Jan. 10, 2008

Related U.S. Application Data (60) Provisional application No. 60/814,995, filed on Jun. 20, 2006.

(51) Int. Cl.
*G06K 9/00* (2006.01)
(52) U.S. Cl. ......................... 382/128; 382/167
(58) Field of Classification Search .................. 382/128, 382/167
See application file for complete search history.

(56) References Cited

U.S. PATENT DOCUMENTS

| | | | | |
|---|---|---|---|---|
| 5,018,531 A | * | 5/1991 | Hartman | 600/587 |
| 5,852,675 A | * | 12/1998 | Matsuo et al. | 382/167 |
| 7,251,362 B2 | * | 7/2007 | Osawa et al. | 382/167 |
| 7,489,816 B2 | * | 2/2009 | Ladjevardi | 382/167 |
| 7,522,767 B2 | * | 4/2009 | Baker et al. | 382/167 |
| 7,522,768 B2 | * | 4/2009 | Bhatti et al. | 382/167 |
| 7,676,080 B2 | * | 3/2010 | Itagaki et al. | 382/162 |
| 2006/0129411 A1 | * | 6/2006 | Bhatti et al. | 705/1 |
| 2007/0053554 A1 | * | 3/2007 | Fayad et al. | 382/128 |
| 2008/0260218 A1 | * | 10/2008 | Smith et al. | 382/128 |
| 2009/0245617 A1 | * | 10/2009 | Bhatti et al. | 382/141 |
| 2010/0123802 A1 | * | 5/2010 | Kim | 348/234 |

FOREIGN PATENT DOCUMENTS

JP     11019050 A  *  1/1999

* cited by examiner

*Primary Examiner* — Bhavesh Mehta
*Assistant Examiner* — Utpal Shah
(74) *Attorney, Agent, or Firm* — E. Victor Indiano; Indiano Law Group (57) ABSTRACT

A method for diagnosing a condition of a patient includes providing a color reference member that includes one reference color thereon. An electronic visual image is obtained of a patient tissue and the at least one reference color on the image. The electronic visual image is processed with the computer by analyzing the colors in the image of the patient tissue and the reference color. This analysis is performed to obtain a standardized color value of the patient tissue. A condition of the patient is diagnosed by using the standardized color value of the patient tissue so obtained.

24 Claims, 8 Drawing Sheets

Scan from Flow Chart 1, the defined and selected areas of interest, including the subject and all background colors from the RBG-photo template of the picture, and obtain their RBG values from the original picture file, in jpg, TIFF or raw format, and calculate their mean values.

Select an RBG color-spacing relation equation. For example, the first order linear equations (1) to (3) used in this invention, and use the background red (R), green (G) and blue (B) (RGB) values corrected (subtracted) by the black background color (RGB) values, all obtained from the RBG-photo template areas selected, to calculate the fractional constraints or ratios of R, G and B in equations (1) to (3), (Ar, Ag, Ab), Br, Bg and Bb) and (Cr, Cg, Cb), with normalization condition of the sum of the resulted red, green and blue values equal to 255 for each R, G, and B color, and the black (RBG) value becomes (0, 0, 0).

Apply the above-obtained fractional constraints or ratios to the (RBG) values, also corrected with the black (RBG) background values, and the equation (1) and (3) to obtain the initial calibrated (RBG) spectrum values of the selected area of interest of the subject.

To obtain the final calibrated (RBG) spectrum values of the selected area of interest of the subject, by normalizing the above initial calibrated (RGB) values using the fractional or ratio factors, for each R, G and B spectrum, obtained by normalizing the background white area (RBG) spectrum values to have a total sum of R, G and B values equals to 765, (255+255+255), from the selected white area of the RBG-photo template.

METHOD AND APPARATUS FOR DIAGNOSING CONDITIONS USING TISSUE COLOR

PRIORITY CLAIM

The present application claims the benefit of priority to Shiu-Shin Chio, U.S. Provisional Application No. 60/814,995, that was filed on Jun. 20, 2006, and which is incorporated herein by reference.

TECHNICAL FIELD OF THE INVENTION

The present invention relates to a method and apparatus for diagnosing a condition of a patient tissue, and more particularly to a method and apparatus for using standardization techniques for standardizing the color in digital images of tissue to aid in the diagnosis of a patient condition base on the color of the tissue.

BACKGROUND OF THE INVENTION

Biological tissue substances are imbued with color that is observable under a visible light. The colors of some substances, such as skin, hair and teeth will often differ widely between individuals, and are used as identifying markers to identify the individual to whom the particular tissue sample belongs.

All colored bio-substances will exhibit the color-based functionalities that one might expect, such as a reflection, transmission and refraction of light of various wave lengths.

The colors of biological tissues are often determined by genetic factors. For example, the fact that a particular individual has brown hair rather than blond hair is a reflection of the genetic make-up of the person's parents whose genetic make-up, along with Mendelian chance conspire to cause the person to be a brunette.

Along with being a genetic marker, the color of a particular biological tissue is often reflective of the state of health of either or both of the tissue itself and the organism from which the tissue came. For centuries, healthcare practitioners have observed the colors of body tissues, such as the color of a person's skin, eyes, lips, tongue, fingernails or toenails to determine whether a person has a particular disease condition. For example, the existence of a yellowish coloration of a person's skin is often indicative of diseases or abnormal conditions of the liver and/or gallbladder. Additionally, people also use facial color changes to identify stress, anger, cold, alcohol over indulgence and other health-related conditions.

Modern medical practice often relies on color changes to diagnose and/or monitor conditions. For example, the progress of skin cancer is often monitored through an observation of color changes of areas of abnormal skin, and the development of abnormal moles or pigmentations, that are employed to identify possible growth of cancerous cells.

One of the difficulties with using color identification is that it is difficult to calibrate the colors observed, so that one can easily compare observed colors against either a known standard, or against subsequent observations. Although sophisticated scientific instruments exist that measure color spectrums of material, most of such known medical instruments are expensive and require a special skill to operate. Most color-based tissue matching operations still rely on matching an observed color of a tissue by comparing it to a color chart to find an appropriate match.

Unfortunately, any such match relies to a large extent on the subjective observations of the viewer, along with being the type of observation to which it is very difficult to attach any quantitative measurements. Further, most such color observations are usually done by "hand", where an observer compares "actual" tissue sample against a particular color chart. As will be discussed below, the difficulties that currently exist in capturing "true color" images make color-based diagnoses that are made from color images (rather than the live tissue), very problematic and unreliable.

For a wide variety of reasons, the color of a tissue sample (or other object) that appears in a photographic image may differ significantly from the actual color (referred to herein as "true color") of the object.

One factor that will cause the image color to vary from the true color is the influence of the lighting condition that existed when the picture was taken. For example, images captured on film that are taken in a room lighted with a fluorescent light, such as is common in most offices, will tend to have a "colder" or "bluer" appearance, whereas images that are taken wherein the ambient light is provided by Tungsten-based light bulb will tend to have a "warmer" coloration that is more biased toward orange and red hues, rather than blue hues.

Another factor that will cause color to vary in an image captured on film is the manner in which the film is "constructed". When creating a color film composition, the film manufacturer strives not only to produce a film that reproduces colors accurately, but one that also reproduces colors in an aesthetically pleasing manner. Because purchasing decisions for film are often made by the purchaser based on the user's perceptions of the pleasingness of the colors of the pictures, film manufacturers will often bias their film products to balance the colors away from the "true colors" into more "pleasing" colors. In this regard, some films have a reputation of being "warm" films because their color balance is to bias their color balance in favor of the warmer colors (red and orange), and away from the colder (blue) colors. Other films are known as "colder films", since their color bias is toward colder, blue colors and away from warmer orange and red colors.

The developing and printing process can also introduce variations in colors. When a film is developed and printed, the technician, or the developer machine will select color balance for a print that may or may not reflect the actual true colors printed. Additionally, factors such as development time, chemical strength, temperature and the like can affect the hue and intensity of the colors shown in the pictures.

The upshot of the foregoing discussion is that it is very difficult, if not almost impossible, to achieve standardized colors when using conventional photography equipment. Since it is very difficult to standardize the color of a particular tissue sample in an image, it is difficult to use an image to analyze the color of the tissue sample to make an accurate diagnosis of the condition of the tissue sample, or more importantly, the condition of the patient from whom the tissue sample was taken.

Further, because of the inconsistency of the way in which colors are reproduced with conventional photograph equipment, it is difficult to track the progress of the condition by tracking changes of the color of a tissue sample shown in the image. It is difficult to track color changes, because a lack of standardization makes it difficult to determine whether a change in the apparent color of a tissue sample has resulted from an actual change in the color of the tissue sample, or rather, resulted from a change in the conditions under which the picture was taken, or a change in which the color was reproduced on the image.

As will be appreciated, those who are employing color to make a diagnosis would prefer to view images wherein the colors of the tissue samples and other contents of the image were standardized, and not subject to change under influence of lighting, development and the like.

To a large extent today, digital photography is replacing traditional film photography as the medium of choice for many photographic applications. Rather than capturing a picture on a film substrate, the image is captured on solid state sensors such as charge coupled devices (CCDs). CCDs consist of integrated circuits that contain an array of linked or coupled light sensitive capacitors. It is also known as a "color capture device". CCDs are often made from C-MOS devices that are complimentary metal-oxides semi-conductors.

Unfortunately, these CCD chips currently in use are not inherently better than film in capturing "true color". One reason that the CCD chips are no better than film is that CCD chips, when capturing an image, are still subject to the vagaries induced by the ambient light in which the image is being captured. Additionally, variations in color from "true color" can be introduced by camera components such as the camera lens materials, coatings used on lenses and the like. Further, the image captured by the CCDs of commercially available cameras usually undergo color "processing" by the cameras. The color processing by such cameras consists of these color images being processed by the software within the camera. Because most cameras are intended for the photographic and graphic arts markets, the camera companies have found that their digital camera products are better received when the output of the image captured by the CCD of the camera is processed so that the colors of the image are balanced and processed to look natural and be vivid and pleasing to the human eyes. As such, the cameras are designed to color bias the image to enhance the beauty of the picture, rather than to adjust the colors of the picture to reflect the true colors of the image. As discussed above, the use of the true colors would most likely create a picture image that was less aesthetically pleasing than one "balanced for beauty".

Unfortunately, those cameras do not allow an image to be captured without this processing; nor is it easy to reverse engineer this processing, as the algorithms and processing methods employed by the camera companies to so process their images are often maintained by the camera companies as trade secrets.

The goals of one performing a colorimetric analysis on a tissue sample are at odds with those desiring beautiful pictures. In order to make an appropriate colorimetric analysis of a color, it is important to be able to compare that color against a known standard, to help determine the differences between the color of a test subject and the color of the known standard. Additionally, if one is performing a colorimetric analysis on a large number of samples, to try to determine data relating to the comparative condition of the various samples, it is important to have the images of all of the test samples shot under generally identical conditions, so that differences in color reflect differences in actual tissue color, rather than reflecting differences in lighting, or color balance induced by the camera or its processor.

It is therefore one object of the present invention to provide a method and apparatus for facilitating the performance of a colorimetric analysis of a tissue sample by enabling the user to obtain a standardized color value of a patient tissue, that can then be used to better analyzing the condition of the patient. Preferably, this method can be performed with software and consumer affordable, commercially available hardware.

SUMMARY OF THE INVENTION

In accordance with the present invention, a method is disclosed for diagnosing a condition of a patient. The method comprises providing a color reference member that includes one reference color thereon. An electronic visual image is obtained of a patient tissue and the at least one reference color on the image. The electronic visual image is processed with the computer by analyzing the colors in the image of the patient tissue and the reference color. This analysis is performed to obtain a standardized color value of the patient tissue. A condition of the patient is diagnosed by using the standardized color value of the patient tissue so obtained.

Preferably, the step of providing the color reference member comprises a step of providing a color reference member having a plurality of color areas, including a red color area, a green color area and a blue color area, along with a black color area and a white color area.

In the preferred embodiment, the step of processing the electronic visual image by analyzing the colors includes the step of analyzing for at least black, white, red, green and blue colors. A numeric value is assigned from 0 to $\Omega$, to each shade of red, green and blue. A value is assigned of (0,0,0) to black and a value of ($\Omega$, $\Omega$, $\Omega$) is assigned to white.

One feature of the present invention is that an electronic visual image of a patient tissue is employed for performing the analysis. The use of an electronic visual image has the advantage of producing a record of the patient tissue that is useable both for archival purposes, and that is capable of being reviewed by other persons at other times. This compares advantageously with the known prior art wherein the color of a sample of tissue is compared by comparing the tissue to a color chart using the technicians "eyes". As will be appreciated, as the color of tissue is likely to change over time (especially when the tissue is living tissue such as skin, etc.), the ability of an analysis on the tissue to be performed at a later date is reduced significantly, if not impaired totally.

Additionally, when prior art tests are used wherein a person visually compares the color of a tissue to a color of a chart, usually the only permanent record that is made of the test are the results of the test, with the raw sample data not being preserved. With the present invention, not only can the results of the test be preserved in the patient's record, but also the raw data (an image of the tissue sample) from which the results were made can be preserved.

Another feature of the present invention is that a color reference member is provided that includes more than one color and preferably at least three colors in addition to black and white. The electronic visual image that is obtained includes information both about the tissue sample, and the color reference member. When the electronic image is analyzed, the analysis includes an analysis of the colors of both the color reference member and of the tissue sample. The colors of the color reference member are analyzed, and compared with the color of the tissue, in order to obtain the standardized color value of the patient tissue.

This feature has the advantage of making a diagnosis of the patient's condition both easier and more reliable. Reliability is enhanced because by standardizing the color of the tissue against a known color sample, the influence of the variations from true color induced in the image by such things as lighting, color balance, and camera programming can be reduced significantly and hopefully, virtually eliminated. Not only does this permit the color of the instant sample to be judged more accurately, but also allows the color of the particular sample (and hence the condition of the patient) to be compared more reliably against other tissue samples taken from other patients, and also other samples taken from the same patient. This advantage becomes especially valuable when one is tracking the progress of a disease. For example, one might seek to monitor the progress of a patient's recovery from a severe sunburn by monitoring the color of the patient's skin during the recovery process.

Prior to the present invention, employing a colorimetric analysis (especially when images are used), was problematic because perceived differences in color and the patient's skin from day to day might be just as likely to be attributable to differences in lighting or camera color bias as the differences were attributable to actual changes in the skin. By helping to reduce the influence of such extraneous factors, the medical practitioner can have a greater faith that differences in color of a tissue that exist in different samples do in fact represent differences in the actual color of the tissue upon which the calorimetric analysis is being performed.

It is also a feature of the present invention that the reference member can include a sizing scale thereon. The sizing scale can be used to provide a known scale for determining the size of a tissue sample of interest, such as the size of a mole.

This feature has the advantage of enabling the medical practitioner to not only determine the color of a particular tissue sample of interest, but also to determine the size of a particular tissue sample of interest. Determining the size of a tissue sample is often important when tracking the size of skin abnormalities, such as moles or discolorations, because the changes in the size of such moles and discolorations are often indicative of an advancing disease state that may impact the aggressiveness with which the disease state or condition is treated by the medical practitioner.

These and other features of the present invention will become apparent to those skilled in the art upon a detailed review of the drawings and detailed description presented below, that represents the best mode of practicing the invention perceived presently by the Applicant.

BRIEF DESCRIPTION OF THE DRAWINGS

FIG. 2A is a more detailed flow chart view of the process of the present invention showing the steps of RGB calibration on the selected area of interest of a test subject with RGB data of all background colors, and in particular, detailing the mathematical standardization process by which a color reference chart can be calibrated in accordance with the present invention;

DETAILED DESCRIPTION

Figure 1A:
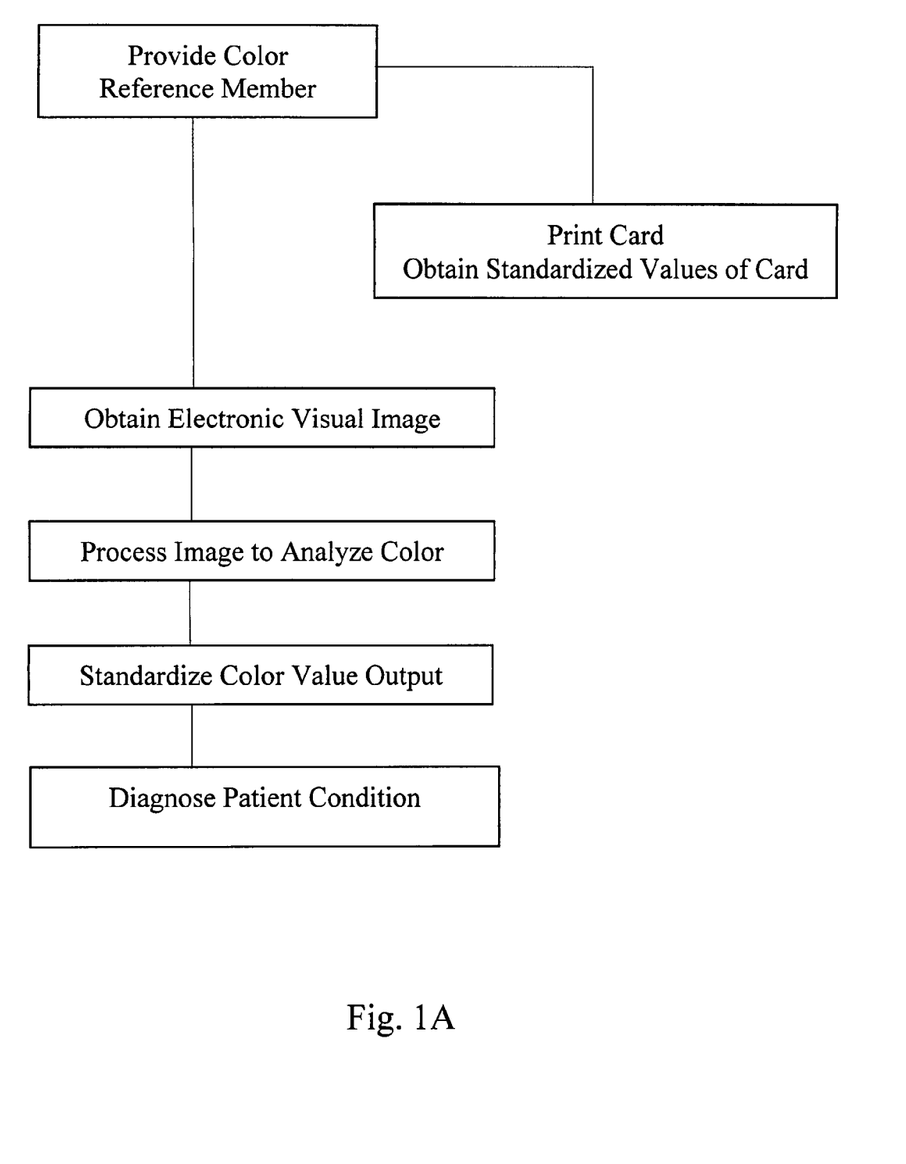
FIG. 1A is a flow chart view of an overview of the process of diagnosing a patient's condition of the present invention.
Figure 1B:
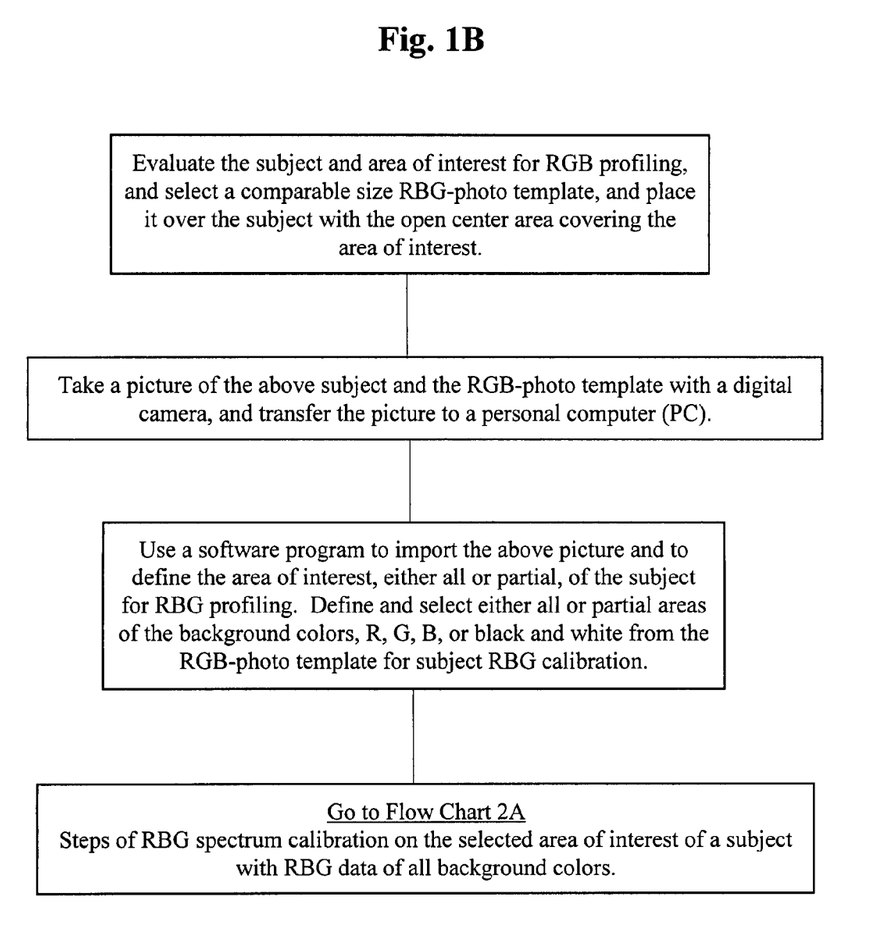
FIG. 1B is a more detailed flow chart view of the process of the present invention showing the steps to obtain a calibrated RGB spectra of a test subject from a digital photo.

In FIG. 1, a flow chart that provides an overview of the process of the present invention is shown.

The first primary step in the process is to provide a color reference member (such as is shown in FIG. 2-6) that includes at least one reference color thereon. Preferably, the color reference member includes a plurality of colors thereon, such as the three colored areas shown in FIG. 1, which actually, includes five colors if one were to include a white area and a black area as "colors". Alternately, color reference cards having a plurality of other different numbers of colors can be used, such as the six color, color charts shown in FIGS. 4 and 6, that include six colors in addition to black and white, for a total of eight "colors".

Prior to the card being used, but after the card is prepared, it may be useful to obtain standardized values of the colors on the card, since the colors on the card are subject to changes from printing to printing. These color values that are obtained should be standardized color values that are obtained under defined and standardized conditions and parameters.

The second step in the process is to obtain an electronic visual image of the tissue sample and the reference color of the color card.

This is obtained by taking a picture of the reference card and the tissue sample within the same frame. If a digital camera is used for capturing the picture, the digital picture itself will comprise the electronic visual image that is thus obtained. However, if a film camera is used, the film should then be developed, and from the developed film an electronic visual image obtained, such as by scanning a print of the printed picture made from the film negative.

Next, the image is processed to analyze the color. Through this analysis process, as will be described below, a standard color value of the patient's tissue is obtained. This standardized color value is obtained by mathematically comparing the colors in the image, and the color of the patient tissue to the known colors of the color reference area.

The output that comprises the standard color value output of the patient tissue can be a numerical value, or can be in the printed image of the color.

Finally, the final step is to use the standardized value color output of the patient's tissue to make a diagnosis of the patient's condition. This diagnosis can be a qualitative diagnosis, that, for example, would denote the presence or absence of a condition (such as jaundice), or could be a quantitative diagnosis that might result in some quantitative or semi-quantitative value that relates to the degree of the condition, such as a degree of jaundice manifested in the tissue sample, or the degree of discoloration caused by a sun burn, mole or melanoma.

Figure 2:
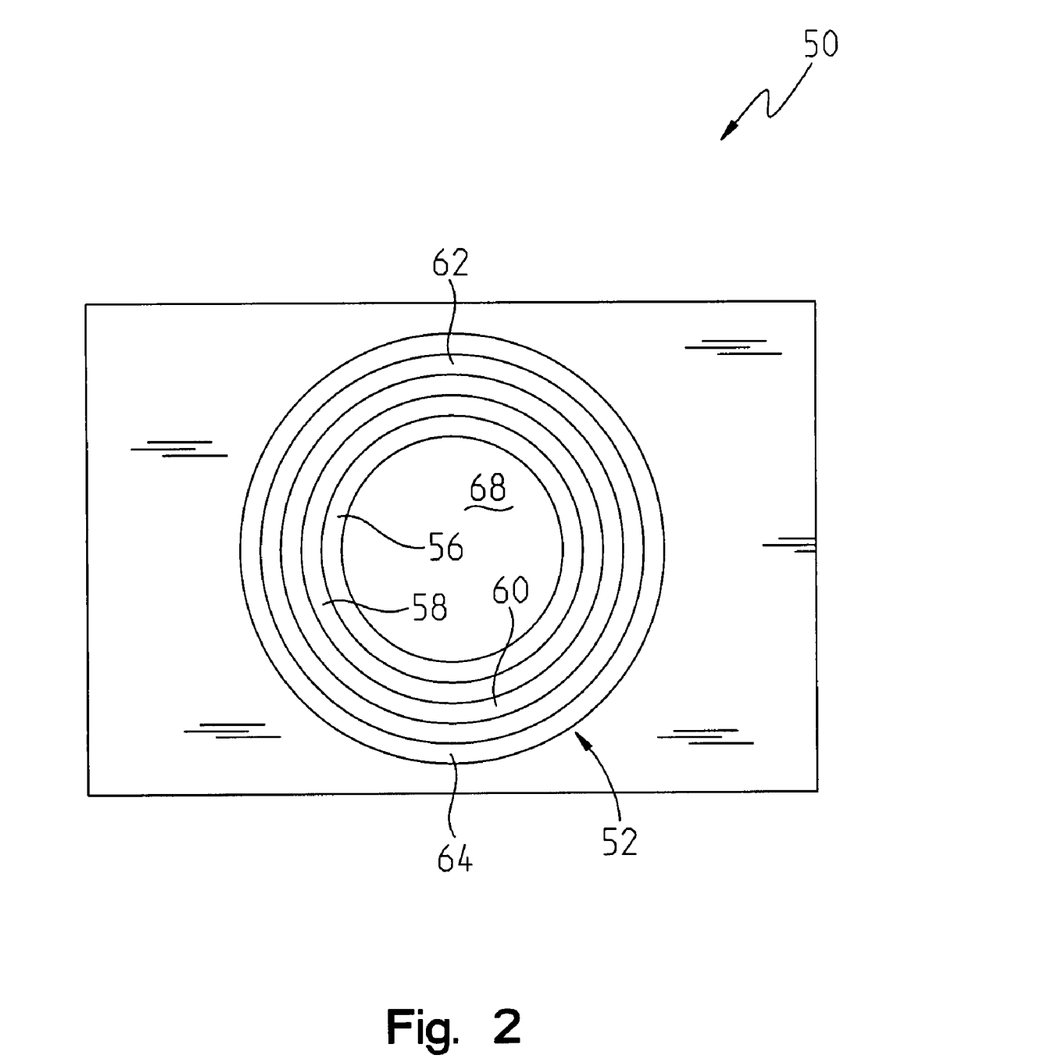
FIG. 2 is a top view of a color reference card useable with the present invention.

Turning now to FIG. 2, an exemplary color reference card 50 is shown and will be discussed. The exemplary color reference card 50 shown in FIG. 2 comprises a thin, card-like element of an appropriate size and shape. The particular size and shape of the card will vary, depending upon its particular use.

The card should have enough surface area so that appropriately sized color areas can be printed on the surface of the card, while permitting enough area for an open tissue receiving aperture, to facilitate the placement of tissue adjacent to the color containing areas, so that the tissue sample and the color containing areas can be contained quite easily within the same image. For many purposes, a color reference card 50 having dimensions of approximately three inches by five inches or four by six inches will work quite well, although smaller, bandage-sized cards might be useful when performing calorimetric analysis of small tissue areas such as teeth and gums, or moles on fingers or toes.

The color reference member, shown as a color reference card 50 of FIG. 2 includes a plurality of color containing areas 52 thereon. The color containing areas 52 on the embodiment of the card 50 shown in FIG. 2 comprise a plurality of concentric color rings. The inner most color ring 56 comprises a first color area that, in the instant example, preferably contains a red color. A second color reference ring 58 is disposed radially outwardly of the first color area 56, and is preferably colored a green color. A third color reference area 60 is disposed radially outwardly and concentrically of the second color area 58. The third color reference area 60 preferably has a blue color. Although the card of FIG. 2 is often referred to as a "three-color card" because it includes three color reference areas including a red area 56, a green area 58 and a blue area 60, card 52 may actually also be referred to appropriately as a "five color area" as it includes a black color reference area 62, and a white color reference area 64, that are also ring-like in shape, and are disposed radially outwardly of the third color reference area 60.

In performing the color calibration of the present invention, all five colors are used to make the calibration, and to provide the standardized color value for the tissue sample.

At the center of the card 50 is a "cut-out" area, that comprises a tissue receiving area, here shown as a tissue receiving aperture 68. The tissue receiving aperture 68 is an open area, adjacent to which tissue can be placed, such as is shown in FIG. 3.

Figure 3:
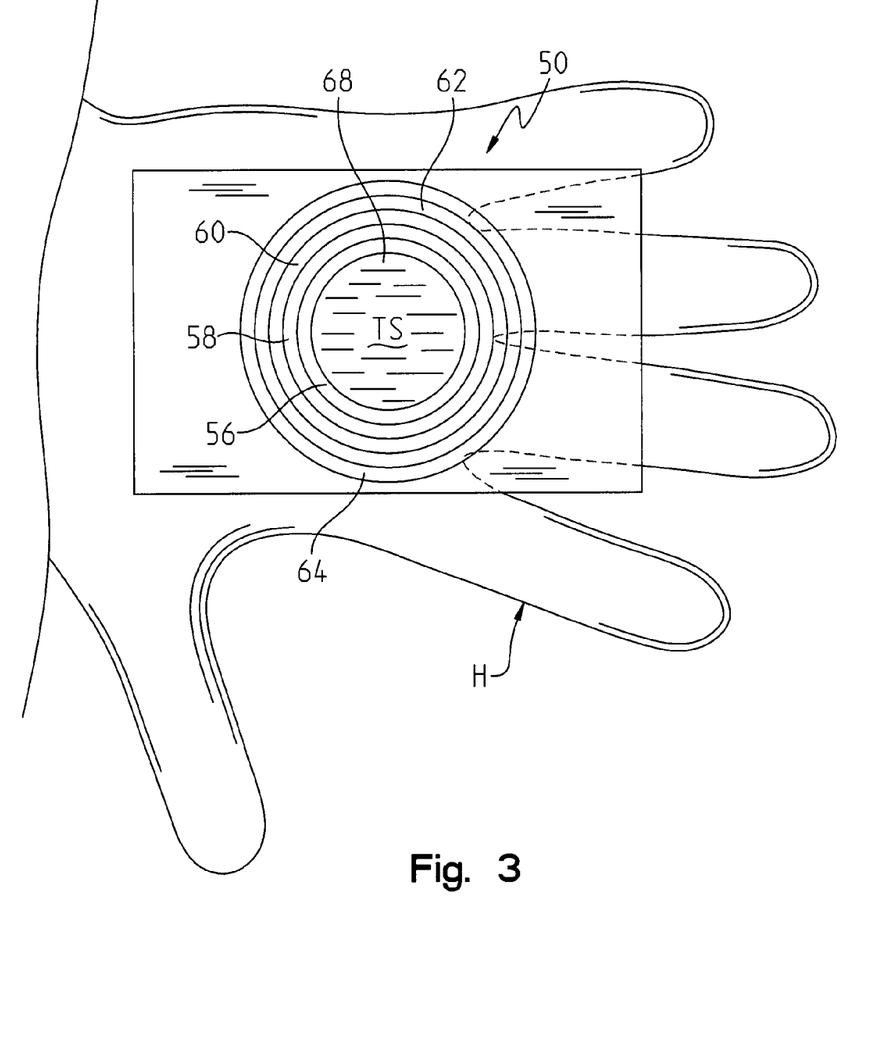
FIG. 3 is a top view of a color reference card showing the card used in connection with a tissue sample.

As shown in FIG. 3, a tissue sample TS is placed within the tissue receiving aperture 68. The tissue sample TS of FIG. 3 comprises a sample of skin tissue that resides on the hand H of a patient.

As is demonstrated in FIG. 3, if one were to take a picture of FIG. 3, one would take a picture of the tissue sample adjacent to a color reference areas 56, 58, 60, 62, 64, so that the tissue sample TS and the color reference areas would all appear within the image, assuming that the image was properly focused and set up to include all of the color areas 56-64 and the tissue sample TS contained within the tissue sample receiving area 68. As shown in FIG. 3, the card is sized to place over the tissue sample, such as by laying the card 50 on the user's hand, so that the tissue sample TS of interest is placed within the aperture 68 that comprises a tissue sample receiving area.

Figure 4:
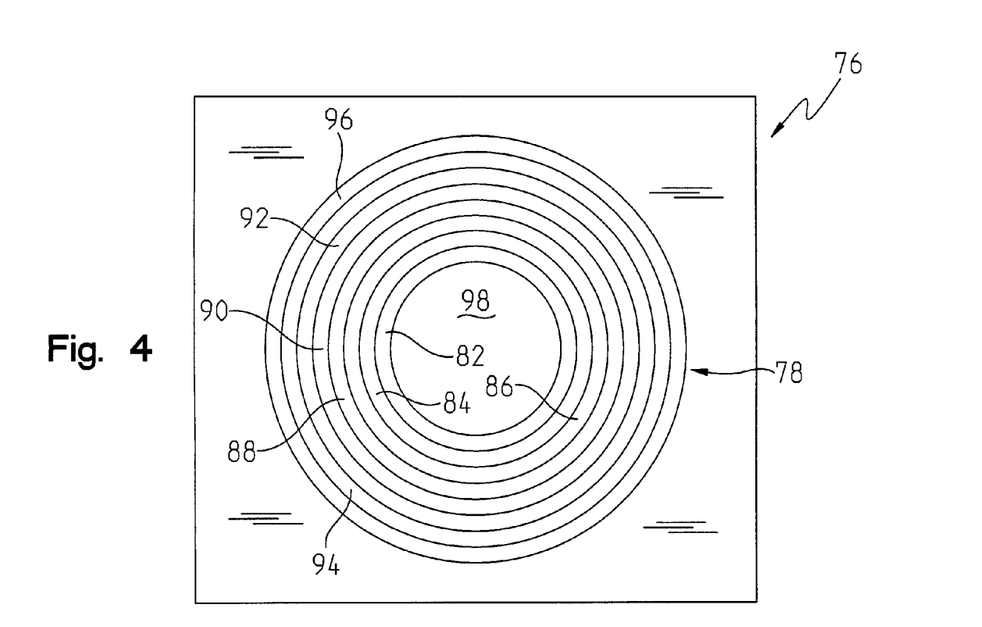
FIG. 4 is an alternate embodiment six color (in addition to black and white) color reference card.

FIG. 4 shows an alternate embodiment color reference card 76, that contains color reference areas having six distinct colors, in addition to black and white.

The card in FIG. 4 is configured generally similarly to card 50 of FIG. 2, insofar as it includes a plurality of concentric rings that comprise the color areas. The color areas 78 of FIG. 4 include a first, or red color area 82, which comprises the inner most ring. Disposed radially outwardly of the red color area 82 is a yellow color area 84, with a green color area 86 disposed radially outwardly of the yellow color area 84. A light blue (light cyan) color area 88 is disposed radially outwardly of the green color area 86, and a blue (cyan) color area 90 is disposed radially outwardly of the light blue color area 88. A light red (light magenta) color area 92 is disposed radially outwardly of the blue color area 90. All of the above-referenced color areas 82-92 are generally ring-shaped in configuration. A black color area 94 is disposed radially outwardly of the light red (light magenta) color area, and a white color area 96 is the outward most ring of the color areas. A tissue receiving aperture 98 is disposed centrally within the color areas 78, and is configured generally similarly to the tissue receiving area 68 of the card 50 of FIG. 2, insofar as it comprises an opened aperture into which the tissue sample of interest can be placed, such as a tissue sample TS shown in FIG. 3.

As alluded to above, a primary difference between the card 76 of FIG. 4, and the card 50 of FIG. 2 is that the card 76 of FIG. 4 uses six different color areas, and six colors, whereas the card 50 of FIG. 2 uses three color areas and three colors (in addition to the black and white color areas used on both).

This use of additional color areas improves the precision and accuracy of the color standardization of the tissue sample, and also likely increases the complexity of the equations and algorithms required to standardize the colors. It is envisioned that certain circumstances will exist where such additional precision rendered by the six colored sample will be desirable and/or necessary, whereas in other cases, the use of the three colors such as that shown in FIG. 2, will be more than sufficient.

The additional three colors used in FIG. 4, that are not found in FIG. 2 include light blue (light cyan), that is placed in color area 88, light red 92 (or light magenta) that is placed in color area 92, and yellow, that is placed in color area 84.

Figure 5:
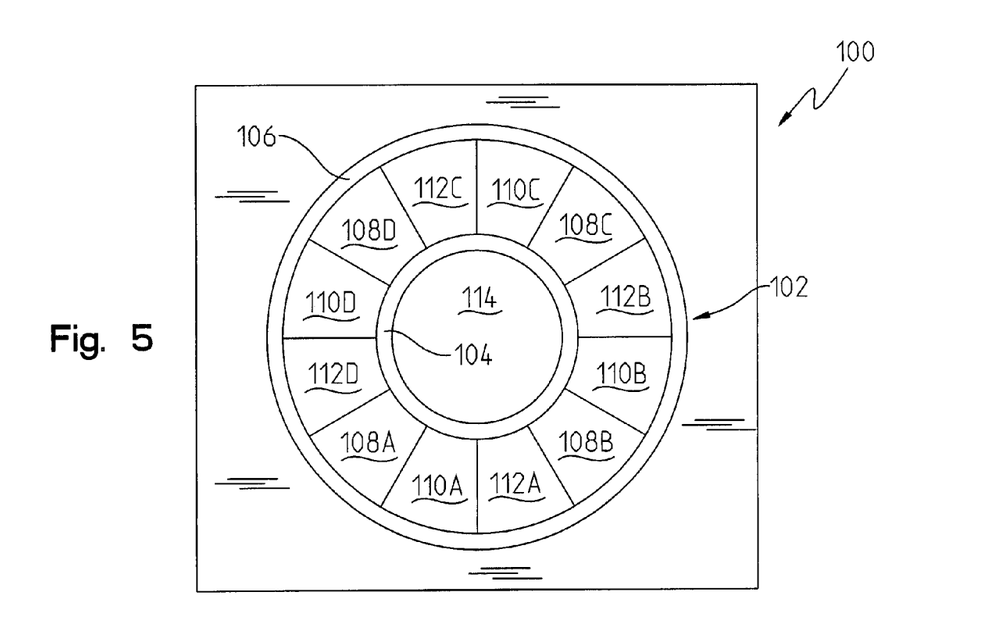
FIG. 5 shows an alternate embodiment four color (plus black and white) color reference card.

Turning now to FIG. 5, another alternate embodiment is shown. The alternate embodiment shown in FIG. 5 comprises a color reference card 100 having a plurality of color reference areas 102, wherein the black 104 and white 106 color areas are ring-shaped, with the red 108, green 110 and blue 112 color areas being truncated pie-shaped areas disposed between the inner black ring 104 and the outer white ring 106.

Color reference card 100 includes four sets of pie-shaped red color areas 108A-108D; four sets of pie-shaped green color areas 110A-110D; and four sets of pie-shaped blue color areas 112A-112D.

This dispersion of the red, green and blue areas helps to ensure that each of the reference red, blue and green colors can be fitted into and become a part of the image made of the card 100 and tissue sample TS, and especially, made a part of the electronic image of the card 100 and tissue sample TS that is used for performing the color analysis of the present invention.

Figure 6:
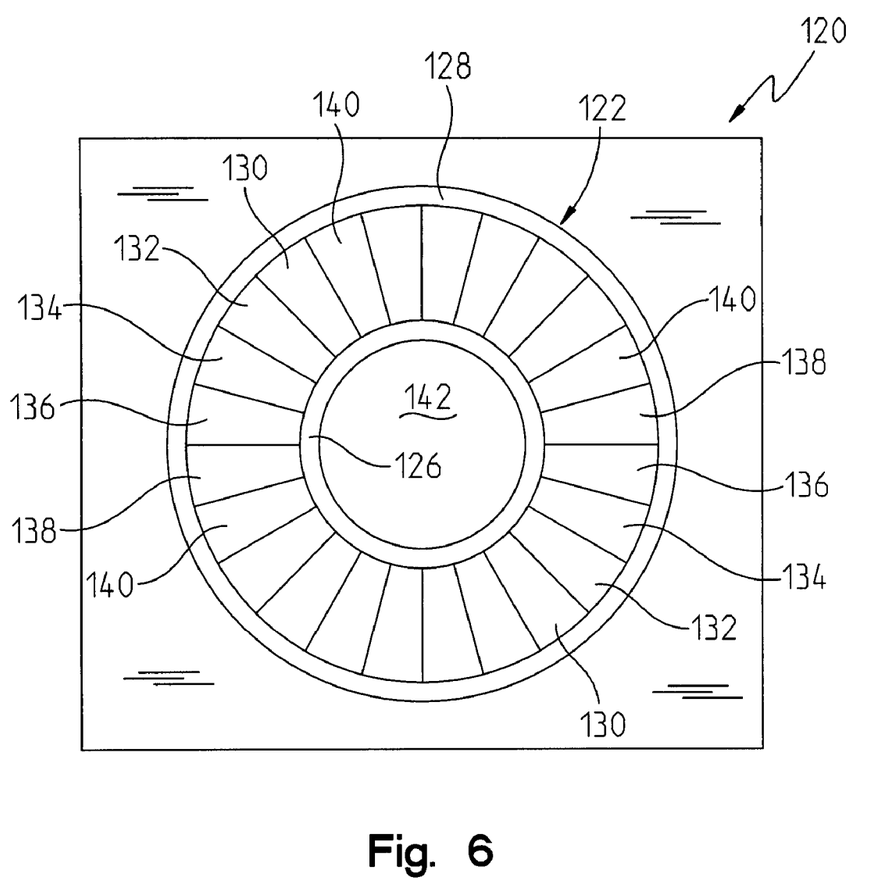
FIG. 6 is an alternate embodiment "pie-shape" six color (plus black and white) color reference color card.

Another alternate embodiment is shown in FIG. 6. The alternate embodiment color reference card 120 of FIG. 6 is constructed generally similar to the color reference card 100 of FIG. 5, except that color reference card 120 of FIG. 6 includes a plurality of color areas that are designed to accommodate a six color reference card, similar to the six color reference card of FIG. 4.

Color reference card 120 includes a plurality of color areas 122, including a ring-shaped interiorly disposed black color area 126, that rings the tissue receiving aperture 142, and an radially outwardly disposed ring-shaped white color area 128. A plurality of pie-shaped color areas 130-140 are disposed between and extended between the black color area 126 and the white color area 140. These color areas include four red (magenta) color areas 130, four light red color areas 132, and four sets of blue color areas 134. Additionally, these color areas include the fourth, light blue color areas (light cyan) 36, four sets of green color areas 138 and four sets of yellow color areas 140. As such, it will be appreciated that the primary difference between the color reference card 120 of FIG. 6, and the color reference card 100 is the inclusion, in color reference card 120 of FIG. 6 of four light red color areas 132, four light blue color areas 136 and four yellow color areas 140.

In order to create standardized colors, it is important to have a "known value" from which one can start, so that one can standardize the "unknown" by comparing it to the known. In the instant case, the "known" is the color on the color areas of the cards, and the "unknowns" are the colors of the color areas of the image of the color areas of the card and the color of the tissue sample both in its natural state, and in its "image".

In order to provide this known, it is believed that it will generally be advantageous to have the color cards manufactured by an approved reference lab or supplier, rather than being printed out on an individual basis by the user. It is preferred that the color reference card be printed by a reference laboratory, or the manufacturer, to ensure that the colors' fidelity on the cards is reliable, and reproducibly similar from card to card.

Differences in individual printers make it difficult to achieve this reproducibility if the cards are printed by individual users. However, it is also possible that the cards may be producible by individuals.

However, factors working against the printing by individuals include such things as differences in inks that are used by individual printers, differences in paper upon which the card will be printed, and other factors that might ultimately result in too significant of a variation between cards printed by different users so as to make individually printed cards valuable as known reference points.

As alluded to above also, it is difficult to maintain color consistency over long periods of time, due to the fact that inks used to print the reference cards and the paper on which the reference cards are printed might vary enough from batch to batch so as to make the colors cards vary from batch to batch of cards that are printed. For most purposes, it is believed that these variations in colors between batches will be insignificant enough to provide a functionally useable degree of reliability and reproducibility between cards of different batches, so long as the card printers employ good quality control measures to ensure uniformity and consistency of ink type, uniformity and consistency of printer type, and uniformity and consistency of paper type.

Nonetheless, certain conditions may exist wherein one wishes to achieve a higher degree of precision by standardizing the reference card itself, to understand how far the reference card itself deviates from ideal or "standard". In order to do this, one would obtain an electronic visual image of the reference color on the reference card under defined conditions and parameters. By capturing such an electronic visual image under defined conditions and parameters, one would try to eliminate as many variables as possible.

One can obtain the electronic visual image by either taking a digital camera picture of the reference colors on the reference card; or otherwise, by scanning the reference colors on the reference card. In either event, an electronic visual image should result. This electronic visual image can be processed by analyzing the colors in the image to obtain the standardized color value of the color reference card under the defined conditions and parameters. The manner in which the electronic visual image is processed and analyzed is basically similar to the manner in which the image of the reference and tissue sample are processed and analyzed, and will be discussed in more detail later.

Information about the standardized color value under the defined conditions and parameters can be provided with the color reference card. For example, a code may be printed on the color reference card, that could be entered into the software of the card processor, so that the standardized color value under the defined conditions and parameters of the particular reference card would be utilized in determining the standardized color value of the patient tissue, through the computer processor using both the obtained value of the reference color in the image and the standardized color value under defined conditions and parameters of the reference card to calculate and determine the standardized color value of the patient tissue.

Alternately, the information about the standardized color value under the defined conditions and parameters of the color reference card could be entered onto a central database, that would correlate with a serial number or other identifying number of the particular color reference card. In order to obtain the standardized color value under the defined conditions and parameters of the color reference card, the user could then access this database through an appropriate web interface, so that the standardized color value was appropriately figured into the calculations made in order to determine the standardized color value of the patient tissue of interest.

In summary it is important to obtain an appropriate color reference member that includes at least one color reference thereon. Preferably, the color reference member is provided with an area of standard red (R), green (G), blue (B), black (BK) and white (W) areas. Black and white areas define the boundary condition for all RGB (red, green blue) and background colors, and are used for obtaining a calibrated RGB spectrum of a selected subject area from an electronic visual image.

One must then obtain an electronic visual image of the patient tissue and the at least one reference color, and preferably, all of the reference colors that are contained on a particular reference card.

Such an image is preferably obtained by taking a picture of the tissue and reference card with a camera that records images electronically, such as a "digital camera". The image collected on the CCD's of the camera will then comprise the electronic image. Alternately, an electronic visual image can be taken by using a film camera. When a film camera is used, a film picture of the tissue sample and color references must be taken, and then developed. The picture may then either be printed out, or may be scanned from a negative with an electronic scanner, so that an electronic (and preferably digital) visual image is made from the film image.

It will be understood that it is preferred to use the digital camera directly, both because it saves processing steps, and also because it saves a "generation" of potential variation that would exist when a film image (first source of potential variation) is later converted into an electronic image (second source of variation).

In digital film processing, red, green and blue colors are often represented by a number that is given an RGB value that consists of three numbers, with each number being somewhere between 0 and $\Omega$, with $\Omega$ representing the number of possible colors minus 1. For example, the red area of the color reference chart can be represented by the numbers 0, 0, 0 to $\Omega$, $\Omega$, $\Omega$, with a color system wherein $\Omega$ plus 1 colors are used.

In most cases, it is believed that an eight bit color spectrum can be used for analyzing the colors of the present invention having 256 colors, where each of the red, green and blue areas can be represented by a number from 0 to 255 (here $\Omega$ would equal 255). Using this convention (that is not the only convention that one can use), the black area is in reference with an RGB value of (0,0,0). By contrast, the white area has an RGB value of (255, 255, 255). Colors such as brown, orange, blue and the like will have RGB values somewhere between the (0, 0, 0) value of black and the (255, 255, 255) value of white.

The preferred method for creating the electronic visual image of the patient tissue and color reference card, is to take a picture of same with a standard digital camera. The digital camera can record the image in either jpg, TIFF, or RAW format or other standard readable picture format for later retrieval by the software.

Although some cameras contain some photo processing capabilities, it is preferred that the image be uploaded onto a computer having an RGB color monitor. Preferably, the color monitor has at least 256 colors, and allows the picture that is uploaded on the computer to be transferred to a photo managing software, such as Adobe Photoshop, or Windows Media, and to have the photos displayed on the monitor.

If the image is created with a scanner, it is best to save the scanned image in a jpg (as opposed to a pdf) format, so that the image can be better managed by the software. For transferring the image from the scanner to the computer, one can employ any one of a number of various software programs, including the scanner image management programs that are provided by the manufacturers of scanners and given to users with the purchase of a scanner.

Once the image is loaded onto the computer, the image is then processed with the computer to analyze the colors and the image of both the colors of the patient tissue sample, and also the reference colors of the color reference card are also analyzed. The background color areas R, G, B, BK and W are then read from the visual image by the software. Their values are obtained in RGB of (Rx', Gy', Bz') and Black in Rblk, Gblk, Bblk.

The first order linear relationships for example are applied among the red, green and blue (RGB) values with correction of the Black area to normalize them to R=(255, 0, 0); G=(0, 255, 0); B=(0, 0, 255); and BK=(0,0,0).

The normalization occurs through the application of the following equations.

$$R = Ar^*(Rx'-Rblk) + Ag^*(Gy'-Gblk) + Bb^*(Bz'-Bblk)$$

$$G = Br^*(Rx'-Rblk) + Bg^*(Gy'-Gblk) + Bb^*(Bz'-Bblk)$$

$$B = Cr^*(Rx'-Rblk) + Cg^*(Gy'-Gblk) + Cb^*(Bz'-Bblk)$$

where (Ar, Ag, Ab), (Br, Bg, Bb) and (Cr, Cg, Cb) are obtained by normalizing [(Rx'-Rblk)+(Gy'-Gblk)+(Bz'-Bblk)] such that $$R + B + G = \Omega$$

Where R, G and B represent the (RGB) values of red, green and blue area respectively. (Ar, Ag, AB), (Br, Bg, Bb) and (Cr, Cg, Cb) were obtained by normalizing [(Rx'-Rblk)+(Gy'-Gblk)+(Bz'-Bblk)] of for each red, green and blue areas (RGB) values to achieve (R+G+B)=255, black area of (RGB) =(0,0,0).

When analyzing the colors, it is also important to make an appropriate selection of the subject photo area. For example, the area contained within the subject photo area to be analyzed should include the "color areas" of the card, such as color areas 56, 58, 60, 62 and 64 of the reference card 50 shown in FIG. 2. However, it is also useful to remove from the analysis those materials outside the color areas or tissue area.

The area selected can range from 100% of the subject photo area down to a single pixel. The subject photo area can be read, scanned and averaged out. The color pixels of the selected area are used to obtain the averaged RGB values of the selected areas, (x'y',z') for example. Once the area is selected for scanning and analysis, the next step is to obtain the calibrated RGB color spectra (x, y, z) of the selected area by using the normalized RGB correlations of equations 1-3 that are obtained above for each of the red, green and blue color.

Once the calibrated RGB color spectra are obtained, the next step is to apply corrections to the calibrated (RGB) values with ratios for R, G and B color from the white area's (RGB) values of (Wr, Wg, Wb) to match to (255, 255, 255) so that the total value (Wr+Wg+Wb) of the white area is equal to (255+255+255). Although the above example discusses the use of the analysis with a 256 color 8-bit system, it will be appreciated that if a greater number of colors are used, the value of white would equal $\Omega$ (the total number of colors)-1.

When the above steps are performed, one should be able to obtain a standardized color value of the patient tissue. From this standardized color value, a diagnosis of a patient can be made more readily, since the standardized value would be more trustworthy than the value whose precision and reliability are questionable due to influences of light and camera programming, as the standardized color value obtained through the application of the instant invention, as described above, helps to minimize or reduce those influences.

As an example and for demonstration purposes, the method of the present invention was practiced upon three sample photographs of a color reference number and tissue sample, reference card 50 and tissue reference sample TS shown in FIG. 3. Three photographs were taken of such an arrangement by commercially available digital camera. A small area (about 10% of the subject area) at or near the center with 10 (RGB) points were taken and averaged, and 4 (RGB) points for each of red, green, blue, black and white areas were taken and averaged for background data.

The calibrated RGB values of the three photos, mean values and the standard deviations are shown in Table 1.

TABLE 1

| Sampling | R | G | B |
|---|---|---|---|
| 1 | 141 | 123 | 102 |
| 2 | 155 | 130 | 106 |
| 3 | 153 | 130 | 103 |
| 4 | 145 | 124 | 103 |
| 5 | 161 | 130 | 100 |
| 6 | 158 | 130 | 102 |
| Mean | 152 | 128 | 103 |
| STD: | 8 | 3 | 2 |
| % | 5% | 3% | 2% |

The above results were statistically analyzed, and demonstrate the improvement in standard deviation (STD), between the standard deviations that were obtained when the reference color and tissue sample colors were not standardized (STD= (6%, 7%, 15%), when compared with the first order or linear calibration approach using the method of the present invention described above, and as reported in Table 1, that shows standard deviations of (5%, 3% and 2%). This reduction in the standard deviation was accomplished with the reference card member software and methodology of the present invention.

It is believed by the Applicant that a further improvement could be achieved if more RGB points were taken in average for the subject area and the background RGB, areas, black areas, and white areas. Additionally, the Applicant believes that the standard deviation could be reduced if a more standardized picture taking conditions were used, with more uniform lighting, along with the use of non-reflected materials for the RGB photo template.

Figure 7:
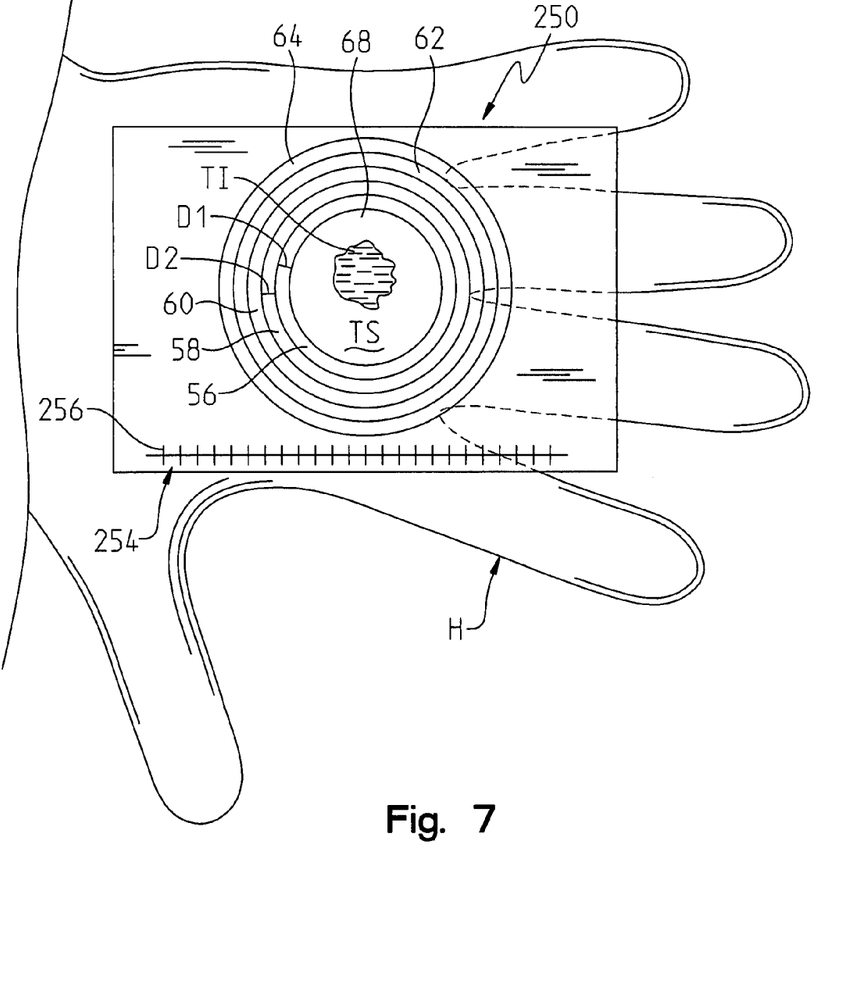
FIG. 7 is a top view of an alternate embodiment color reference card containing a sizing scale, and showing the card used in connection with a tissue sample.

Turning now to FIG. 7, an alternate embodiment reference card 250 is shown. Card 250 is generally similar to card 50 as card 250 includes a plurality of concentric rings 56-64 of different colors (red, green, blue, black and white) that serve as color reference areas. An open area 268 is formed in the center of the card 250, interiorly of the rings and comprises an open aperture into which a tissue sample TS can be placed.

The purpose of reference card 250 is to illustrate how the reference card 250 can be used to determine the size of a tissue sample of interest TI, such as a mole or a melanoma, wherein the size of the tissue sample of interest TI is of some importance to the patient or medical practitioner.

It will be noted that reference card 250 does include a scale 254 printed thereon that includes a plurality of gradations 256 that are disposed at known intervals. By comparing the width (for example), of the tissue of interest TI against the number of gradations encompassed by the width of the tissue of interest TI, one can determine the size of the tissue of interest TI.

However, the scale 254 is not the only method by which size can be determined. The diametric widths (e.g. D1, D2) of the color area rings 56, 58 can be set to be a known and predetermined size. By comparing the size of the tissue sample of interest TI to the diametric width (D1, D2, etc.) of the rings, one can also determine the size (e.g. width) of the tissue of interest TI.

It will also be appreciated that the various sizes of the color areas of the other cards found in FIGS. 1-6 can also be made to have a known size to enable one to determine the size of a tissue of interest, by comparing and analyzing the size of a tissue of interest against the size (such as the diameter width) of the rings 56, 58. This can be done by comparing the size on the electronic image taken of the card and the tissue of interest.

To process the electronic visual image, the procedure described above relies primarily upon the normalization of the values obtained in RGB according to a linear relationship. As demonstrated from the data achieved in Table 1 above, this linear relationship is believed by the Applicant to be representative enough and accurate enough for many purposes, to achieve more normalized color value for the tissue sample, that will suffice for most purposes. However, the color spectrum RGB space relationship in general, may not be linear, and may require higher order curve fitting or a polynomial curve fitting to approach a level of accuracy that would be closer to 100%. To achieve such a higher accuracy, it would also be useful, if not necessary, to employ a color reference card that includes a wider variety of colors than just the three color, red, green, blue (and black and white) colors used in the reference cards shown in FIGS. 2, 3.

As discussed above, FIGS. 4 and 6 show examples of six color RGB photo template color reference cards, which in addition to the primary colors of red (255, 0, 0); green (0, 255, 0); and blue (0, 0, 255) colors, colors of yellow, light blue and light red are employed. The particular colors that are employed are a yellow (Y) with an RGB value of (255, 255, 0); light blue (also known as light sion) that has an RGB value of (0, 255, 255); and light red (LR) which is also known as light magenta that has an RGB value of (255, 0, 255). These three colors were added to the color reference chart. When using this six color RGB photo template color reference card, a second order curve fitting method was applied to define the color space or calibration of colors of the subject. Although it is possible to achieve even a higher accuracy with this second order curve fitting, it may not be practical or necessary to achieve a higher accuracy for general applications.

Other improvements in the accuracy of the color spectrum, calibration and standardization of the present invention is possible by employing more than six colors on the RGB photo screen reference card, and using higher than second order curve fitting, and/or by using higher than an 8-bit color resolution.

Although the templates shown in the figures are generally card-like and work well with for skin tissue samples, it will be appreciated that specialized templates and photographic techniques might be used to photograph other tissue samples. For example, a more flexible and smaller card, having a small tissue sampling area might be useful when obtaining tissue sample pictures of a tooth or eye. Additionally, because of its sensitivity to light, it may be advisable not to employ flash-lighting system when taking pictures of an eye for use in connection with the present invention.

As alluded to above, the present invention can be used in connection with diagnosing a wide variety of conditions, where the color of body tissue is often important in determining the existence of a particular condition or abnormality, or in some cases, the degree of severity of the particular abnormality.

There are a plurality of conditions with which the method and apparatus of the present invention can be used. One example is that the present invention can be used in connection with the monitoring and diagnosing of skin abnormalities, such as cancer cell growth, and evaluation of burns, and sunburn.

Additionally, monitoring the color of certain body tissues may have a usefulness in connection with the diagnosis of patient conditions that are performed according to traditional Chinese medical practices that correlate the color of the human body, such as the tissues of the face, eyes, nails, tongue and other body parts to disease problems with major organs, such as the heart, liver and kidney.

The present invention may also have utility in diagnosing cardiovascular related issues such as eye blood pressure and eye problems.

Within the cosmetic realm, the apparatus and method of the present invention could be used to help match prosthetic body parts to the natural color of existing body parts, such as matching the color of crowned teeth to the particular user's natural teeth. Additionally, the present invention could also be used for color matching with other prosthetic parts.

Although the Applicant has disclosed the best of mode of practicing the invention perceived presently by the Applicant, it is to be understood that specific disclosed embodiments are by way of example and not limiting. Consequently, the reader will understand that variations and modifications exist within the scope and spirit of the present invention. It is intended that the appended claims be construed to include alternative embodiments to the extent permitted by the prior art.

What is claimed is:

1. A method for diagnosing a condition of a patient comprising:
   (1) providing a color reference member that includes an open area portion for receiving a patient tissue and at least a first, a second and a third reference color thereon disposed on the reference member in, respectively, at least a first, second and third concentric rings least partially surrounding the open area portion,
   (2) obtaining an electronic visual image of the patient tissue disposed within the open area and the at least one reference color of the color reference member that at least partially surrounds the patient tissue,
   (3) processing with a computer, the electronic visual image by analyzing the colors, in the image, of the patient tissue and the reference color to obtain a standardized color value of the patient tissue; and
   (4) diagnosing a condition of the patient by using the standardized color value of the patient tissue.

2. The method of claim 1 wherein the first, second and third reference colors include at least a red color, a green color and a blue color disposed on the respective first, second and third concentric rings.

3. The method of claim 2 wherein the color reference member includes a white color area and a black color area.

4. The method of claim 2 wherein the step of providing the color reference member includes the step of providing a color reference and having a tissue receiving area capable of receiving a patient tissue in an open area portion fully interiorly disposed within at least one of the plurality of color areas.

5. The method of claim 1 wherein the step of processing the electronic visual image by analyzing the colors includes the step of
   (a) analyzing for at least black, white, red, green and blue colors;
   (b) assigning a numeric value to each shade of red, green and blue in the form of a linear matrix, the numeric value falling within a range between a minimum value to and a maximum value;
   (c) assigning the minimum value for each of red, blue and green to black, and
   (d) assigning the maximum value for each of red, blue and green to white.

6. The method of claim 5 wherein the step of processing the electronic visual image by analyzing the colors includes the step of
   (a) obtaining the values in RGB of visual image in the format (Rx', Gy', Bz'), where
      Rx' is the value of the shade of red in the image,
      Gy' is the value of the shade of green in the image, and
      Bz' is the value of the shade of blue in the image, and
   (b) obtaining the value of the black areas in the image (Rblk, Gblk, Bblk).

7. The method of claim 6 wherein the step of processing the electronic visual image by analyzing the colors includes the step of obtaining the standardized color value of the patient tissue, including the step of normalizing the values obtained in RGB according to the linear relationship:

$$R = Ar^*(Rx'-Rblk) + Ag^*(Gy'-Gblk) + Bb^*(Bz'-Bblk)$$

$$G = Br^*(Rx'-Rblk) + Bg^*(Gy'-Gblk) + Bb^*(Bz'-Bblk)$$

$$B = Cr^*(Rx'-Rblk) + Cg^*(Gy'-Gblk) + Cb^*(Bz'-Bblk)$$

where (Ar, Ag, Ab), (Br, Bg, Bb) and (Cr, Cg, Cb) are obtained by normalizing [(Rx'−Rblk)+(Gy'−Gblk)+(Bz'−Bblk)]
such that $$R+B+G=\Omega.$$

8. The method of claim 5 wherein the step of assigning the numeric value to each shade of red, green and blue in the form of a linear matrix, wherein the numeric value falls within a range between a minimum value and a maximum value comprises the step of assigning a numeric value of the minimum value at (0, 0, 0) and the maximum value at (255, 255, 255) on a three axis, 256 color, eight bit scale.

9. The method of claim 8 wherein the value of (255, 255, 255) is assigned to white.

10. The method of claim 5 wherein the first, second and third reference colors include at least a red color, a green color and a blue color disposed on the respective first, second and third concentric rings.

11. The method of claim 1 wherein the step of providing the color reference member including the step of
   (a) providing a color reference card,
   (b) obtaining an electronic visual image of the reference color on the reference card, under conditions and parameters,
   (c) processing the electronic visual image by analyzing the colors in the image to obtain a standardized color value of the color reference card under defined conditions and parameters,
   (d) providing information about the standardized color value under the defined conditions and parameters with the color reference card.

12. The method of claim 11 wherein the step of processing the electronic visual image includes the step of
   (a) analyzing the colors of the reference color in the image to obtain a value of the reference color in the image;
   (b) using both the obtained value of the reference color in the image and the standardized color value under defined conditions and parameters to obtain the standardized color value of the patient tissue.

13. The method of claim 12 wherein the step obtaining the standardized color value of the patient tissue includes the step of obtaining a numeric standardized value of the patient tissue.

14. The method of claim 1 wherein the step of obtaining the standardized color value of the patient tissue includes the step of obtaining a standardized numeric color value of the patient tissue by comparing color of the patient tissue with both a value of the reference color of the image, and a value of the reference color of the color reference member obtained under defined conditions and parameters.

15. The method of claim 1 wherein the step of providing the color reference member includes the step of providing a color reference member having a tissue receiving open portion disposed internally of the color reference rings for facilitating placement of a patient tissue adjacent to the reference color of the color reference member.

16. The method of claim 1 wherein the step of providing the color reference member includes the step of providing a color reference member having the first, second and third concentric rings color rings surrounding the open area portion that comprise, at least a first red color ring, a second green color ring a third blue color ring a white color area and a black color area.

17. The method of claim 1 wherein the step of obtaining an electronic visual image of a patient tissue includes the step of obtaining an electronic visual image of a first reference patient tissue, and a second test sample patient tissue.

18. The method of claim 17 wherein the step of processing the electronic visual image includes the step of analyzing the colors in the image of the first reference patient tissue, the second test sample patient tissue and the reference color to obtain standardized color values of the first reference patient tissue and the second test sample patient tissue; and
   the step of diagnosing a condition of the patient includes the step of diagnosing the condition of the patient by comparing the standardized color value of the first reference patient tissue and the second test sample patient tissue.

19. The method of claim 1 wherein the the at least first, second and third concentric rings least partially surrounding the open area portion include having a black color area, a white color area, and at least six additional color areas, including a red color ring, a blue color ring, a yellow color ring, a light blue color ring and a light red color ring.

20. The method of claim 1 wherein the step of processing the electronic visual image by analyzing the colors includes the steps of
   (a) analyzing for at least black, white, red, green and blue colors;
   (b) assigning a numeric value from 0 to $\Omega$ to each shade of red, green and blue; and
   (c) using a first order linear relationship to normalize the values obtained.

21. The method of claim 1 wherein the step of processing the electronic visual image by analyzing the colors includes the step of
   (a) analyzing for at least black, white, red, blue and green colors;

(b) assigning a numeric value from 0 to Ω to each shade of red, green and blue; and (c) using at least one of a second order linear relationship, a polynomial relationship and an Nth order linear relationship to normalize the values obtained.

22. The method of claim 1 wherein the step of providing the color reference member includes the step of providing a color reference member having a sizing scale thereon, the step of diagnosing a condition of a patient includes the step of using the sizing scale to determine the size of the patient tissue.

23. A method of diagnosing a condition of a patient comprising (1) providing a reference member that includes an open area portion for receiving a patient tissue and at least a first, a second and a third reference color thereon disposed on the reference member in, respectively, at least a first, second and third concentric rings at least partially surrounding the open area portion, and sizing scale thereon adjacent to and surrounding the open area portion;

(2) obtaining an electronic visual image of a patient tissue at the sizing scale and the at least one reference color of the reference member that at least partially surrounds the patient tissue;

(3) processing, with a computer, the electronic visual image by comparing the size of the patient tissue and the sizing scale to obtain a value for the size of the patient tissue; and (4) diagnosing a condition of a patient by using the obtained value of the size of the patient tissue.

24. The method of claim 23 wherein the step of providing the reference member that includes a sizing scale includes the step of providing a color reference member having a plurality of color reference areas thereon, wherein the color reference areas are of a known size for permitting the color areas to serve as the sizing scale.

* * * * *